United States Patent [19]

Fukuda

[11] 4,361,581

[45] Nov. 30, 1982

[54] SKIN-BEAUTIFYING COSMETIC COMPOSITION

[75] Inventor: Yasuaki Fukuda, 529, Kiyomizu, Okuradani, Akashi-shi, Japan

[73] Assignees: Yasuaki Fukuda, Akashi; Yakurigaku Chuo Kenkyusho, Tokyo, both of Japan

[21] Appl. No.: 221,007

[22] Filed: Dec. 29, 1980

[51] Int. Cl.³ .................. A61K 7/40; C07C 69/02; C07C 69/22

[52] U.S. Cl. .................. 424/312; 424/311; 424/331; 560/231; 260/410

[58] Field of Search .................. 560/231; 568/375; 260/410 R; 424/311, 312, 331

[56] References Cited

PUBLICATIONS

*Quarterly Reviews*, vol. V, No. 2, 1951, pp. 103 and 115, Cook et al., "The Tropolones".

*Primary Examiner*—John F. Terapane
*Assistant Examiner*—F. J. Moezie
*Attorney, Agent, or Firm*—Armstrong, Nikaido, Marmelstein & Kubovcik

[57] ABSTRACT

4-Isopropyltropolone having the formula:

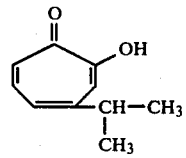

and/or the fatty acid esters thereof having the formula:

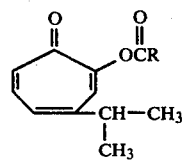

(wherein R is a hydrocarbon group having 1 to 18 carbon atoms) have the excellent skin-beautifying and anti-suntan effects and are usable as active ingredients for the skin-beautifying cosmetics. The fatty acid esters of 4-isopropyltropolone are novel substances.

6 Claims, 2 Drawing Figures

SKIN-BEAUTIFYING COSMETIC COMPOSITION

BACKGROUND OF THE INVENTION

1. Field of the Invention

This invention relates to a skin beautifying cosmetic composition, more particularly a skin beautifying cosmetic composition containing 4-isopropyltropolone and/or fatty acid esters thereof as active ingredients.

2. Description of the Prior Art

It is an eternal wish common to womankind to have a fair and beautiful skin, and a variety of cosmetic preparations blended with the peroxides such as hydrogen peroxide, zinc peroxide, magnesium peroxide, sodium peroxide, zinc perborate, magnesium perborate, sodium perborate, etc., have been offered to live up to such feminine desire. However, the peroxides such as mentioned above had the problems in keeping quality, physical or chemical stability and blending compatibility with the cosmetic compositions, and also their skin-beautifying effect was unsatisfactory. There have been developed and commonly used lately the cosmetics blended with vitamin C, cystine, colloidal sulfur and the like, but even these cosmetics can not still be deemed satisfactory in keeping quality, stability and beautifying effect.

SUMMARY OF THE INVENTION

An object of this invention is to provide an improved skin-beautifying cosmetic composition.

Another object of this invention is to provide the novel fatty acid esters of 4-isopropyltropolone which can be used as active ingredient for the skin-beautifying and whitening cosmetic preparations.

As a result of extensive studies in search for a cosmetic agent which has no side effects unfavorable to the human body and yet can produce the excellent skin-beautifying and suntan preventive effects, this inventor found out the new facts that 4-isopropyltropolone having the formula:

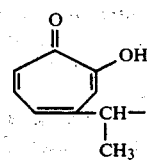

and/or the fatty acid esters thereof having the formula:

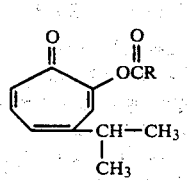

(wherein R is a hydrocarbon group having 1 to 18 carbon atoms) can produce a marvelous skin-beautifying effect as well as a splendid suntan preventive effect as they have an inhibitory action against activity of tyrosinase existing in the human skin to show a prominent suppressive action against growth of melanin as well as high ultraviolet absorptivity, and they also have high stability to pH, light and heat and excellent shelf stability, and that particularly the fatty acid esters of 4-isopropyltropolone have excellent oil solubility and, when blended in a cream or such, they are easily dissolved in the oil layer to show extremely high skin absorptivity, and further, they are not incentive to the skin.

DESCRIPTION OF THE PREFERRED EMBODIMENTS

Figure 1:
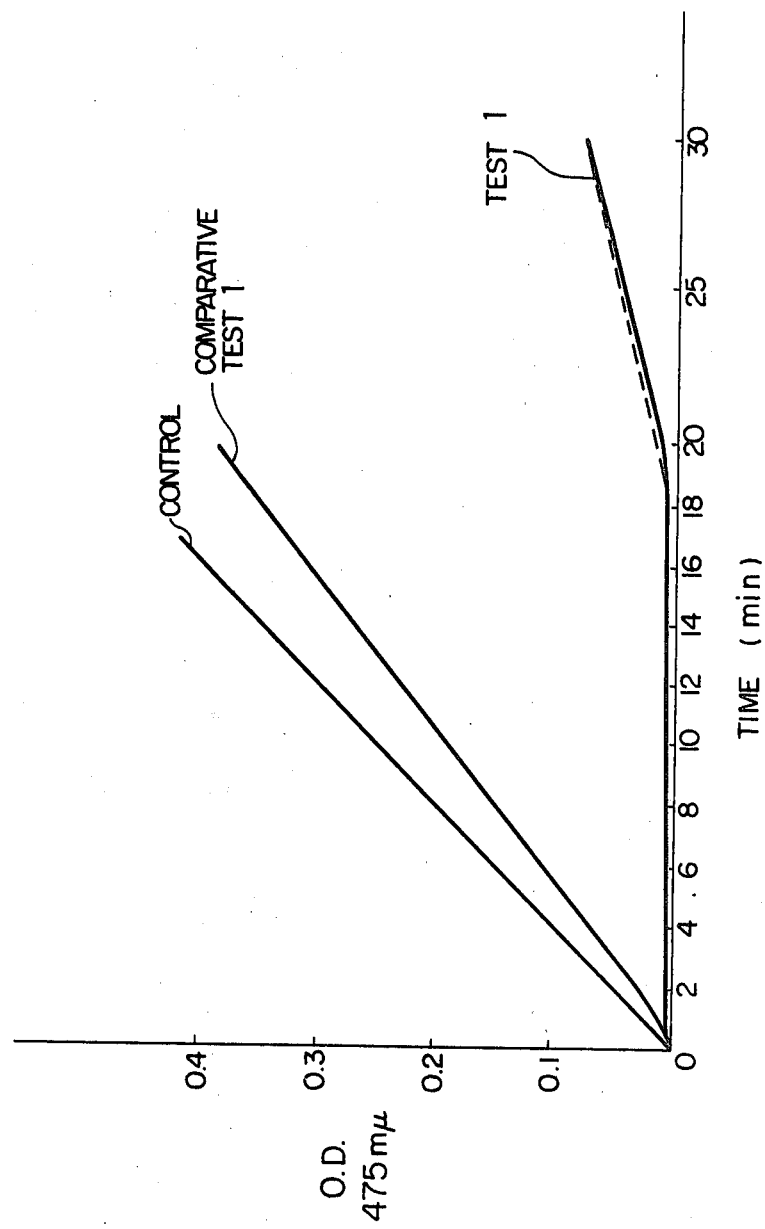
FIG. 1 is a graph showing the relation between degree of pigmentation and time for illustrating the tyrosinase activity inhibiting ability of the liniment obtained in Test 1.

The skin-beautifying cosmetic composition of this invention has as its active ingredients 4-isopropyltropolone and/or a fatty acid ester thereof blended in a base, and these active ingredients are usually contained in an amount of about 0.0001 to 10% by weight, preferably about 0.001 to 5% by weight. A well satisfactory skin-beautifying effect and anti-suntan effect are provided from the said range of content of the active ingredients, but it should be noted that if said active ingredients are contained in excess of 10%, no corresponding merit is derived, while if the content is less than 0.0001%, some suspicion arises over the intended effects of the composition.

In case the active ingredient is 4-isopropyltropolone, if its activity site is blocked by a metal, it loses its tyrosinase activity inhibitory action. In fact, in the presence of 1 ppm of $Fe^{3+}$, 23.51 ppm of 4-isopropyltropolone is deprived of its tyrosinase activity inhibitory action, and likewise, in the presence of 1 ppm of copper $Cu^{2+}$, 13.78 ppm of 4-isopropyltropolone loses its tyrosinase activity inhibitory action. In order to eliminate obstruction by such metal ions against the tyrosinase activity inhibitory action, it is suggested to add a sequestering agent (chelating agent) such as EDTA in an amount of approximately 0.01 to 0.05% (based on the total weight of the composition).

The fatty acid esters of 4-isopropyltropolone according to this invention can be produced, for example, by adding a chloride of a fatty acid to 4-isopropyltropolone in the presence of pyridine.

As for the fatty acids used for the esterification reaction with 4-isopropyltropolone in this invention, there are employed those having 2 to 19 carbon atoms, the typical examples thereof being butyric acid, caproic acid, caprylic acid, lauric acid, myristic acid, palmitic acid, stearic acid and oleic acid.

The thus obtained fatty acid esters of 4-isopropyltropolone are the novel substances. Among these esters, stearic acid ester and palmitic acid ester are most preferred for use as active ingredient for the skin-beautifying cosmetics.

As described above, the present invention finds optimal applications as a skin-beautifying agent and anti-suntan agent, and thus the skin-beautifying cosmetic composition of this invention containing said 4-isopropyltropolone or a fatty acid ester thereof as active ingredient has eliminated the inherent defects of the conventional cosmetic preparations of this type and is not subject to any restrictions by the cosmetic base used and other factors. Therefore, in this invention, all sorts of heretofore used cosmetic base materials such as, for example, various kinds of alcohols, animal or vegetable fats, surfactants, pectin, carboxymethyl cellulose, alginates, etc., as well as other additives such as stabilizer, pigment, aromatic, etc., may be suitably blended, and if desired, the blend may be melted by heating or may be melted and stirred. The composition of this invention can be used in these and all other considerable forms.

The skin-beautifying cosmetic preparations according to this invention are further described hereinbelow by citing their synthesis examples, test examples and prescriptions.

SYNTHESIS EXAMPLE 1 (2-palmitate of 4-isopropyltropolone)

16.4 g of 4-isopropyltropolone was dissolved in 300 ml of pyridine and the mixture was stirred at room temperature and further added with 27.5 g of palmitoyl chloride. After passage of 10 minutes, the mixture was heated to 70° C. for 30 minutes and then allowed to cool by itself to 0° C. for one hour.

The filtrate, from which the precipitated crystals of pyridine hydrochloride had been removed, was concentrated and evaporated to dryness under reduced pressure, and the residue was added with 300 ml of water and stirred at room temperature for 10 minutes to elute the pyridine hydrochloride. Then the insoluble matter was gathered, dried and recrystallized twice from ethanol, whereby there was obtained 32.2 g of white crystals (yield: 80.0%). This product is 2-palmitate of 4-isopropyltropolone.

Melting point: 27°–28° C.

IR (KBr): 1760 cm$^{-1}$ (C=O); 1660 cm$^{-1}$ (C=O).

Elemental analysis: Calculated: C, 77.61; H, 10.45; Found: C, 77.12; H, 10.42.

0.1 g of this product was dissolved in 10 ml of ethanol and this solution was probed by T.L.C. (developer: ether/benzene/ethanol/acetic acid = 40/50/2/0.2; color producing reagent: ferric sulfide). One spot was detected at Rf=0.924.

SYNTHESIS EXAMPLE 2 (2-butyrate of 4-isopropyltropolone)

16.4 g of 4-isopropyltropolone was dissolved in 300 ml of pyridine and the mixture, while cooled with ice, was added with 10.66 g of n-butyryl chloride under stirring, heated at room temperature for 30 minutes and then allowed to cool naturally to 0° C. for one hour. This mixture was then treated similarly to Synthesis Example 1 to obtain 17.57 g of white crystals (yield: 75%). This product is 2-butyrate of 4-isopropyltropolone.

IR (KBr): 1763 cm$^{-1}$ (C=O); 1658 cm$^{-1}$ (C=O).

Elemental analysis: Calculated: C, 71.17%, H, 7.74%; Found: C, 71.10%; H, 7.71%.

SYNTHESIS EXAMPLE 3 (2-caprylate of 4-isopropyltropolone)

16.4 g of 4-isopropyltropolone was dissolved in 300 ml of pyridine and then further added with 16.27 g of capryl chloride while cooled with ice and under stirring, and the resulting mixture was treated after the manner of Synthesis Example 1 to obtain 21.78 g of white crystals (yield: 75%). This product is 2-caprylate of 4-isopropyltropolone.

IR (KBr): 1765 cm$^{-1}$ (C=O); 1660 cm$^{-1}$ (C=O).

Elemental analysis: Calculated: C, 74.44%; H, 9.37%; Found: C, 74.25%; H, 9.26%.

SYNTHESIS EXAMPLE 4 (2-acetylate of 4-isopropyltropolone)

16.4 g of 4-isopropyltropolone was dissolved in 300 ml of pyridine, then added with 7.85 g of acetyl chloride under ice cooling and stirring and subjected to the same treatment as in Synthesis Example 2 to obtain 16.5 g of white crystals (yield: 80%). This product is 2-acetylate of 4-isopropyltropolone.

Elemental analysis: Calculated: C, 69.88%; H, 6.84%; Found: C, 69.48%; H, 6.82%.

SYNTHESIS EXAMPLE 5 (2-stearate of 4-isopropyltropolone)

16.4 g of 4-isopropyltropolone was dissolved in 300 ml of pyridine, added with 30.3 g of stearoyl chloride under stirring at room temperature and treated according to Synthesis Example 1 to obtain 35.0 g of white crystals (yield: 80.0%). This product is 2-stearate of 4-isopropyltropolone.

Melting point: 39°–40° C.

Elemental analysis: Calculated: C, 78.08%; H, 10.77%; Found: C, 78.00%; H, 10.78%.

Rf (measured in the same way as in the case of palmitate): 0.941.

TEST EXAMPLE 1

0.05 g of 4-isopropyltropolone was dissolved in a 30% ethanol-water mixture, and then 0.03% of EDTA was added and dissolved therein. After adjusting pH of the solution by using succinic acid and potassium carbonate, water was added thereto to make the total amount 100 parts. There was obtained a liniment with a 4-isopropyltropolone concentration of 0.05%.

The tyrosinase activity inhibiting ability of the thus obtained liniment was examined in the following way.

1 ml of an L-tyrosine solution (0.3 mg/ml), 1 ml of MacIlvaine's buffer (pH 6.8) and 0.9 ml of said liniment were added into a test tube and incubated in a 37° C. temperature-controlled water bath for 10 minutes. The mixture was then added with 0.1 ml of a tyrosinase solution (0.3 mg/ml) and stirred well, and then immediately a spectrophotometer was set and the absorbance at 475 m$\mu$ was measured with passage of time. As control, a similar mixed solution was prepared by using a 30% ethanol solution instead of said liniment and its absorbance was measured in the same way.

COMPARATIVE TEST EXAMPLE 1

A 0.05% concentration liniment was prepared in the same way as Test Example 1 except for use of colchicine instead of 4-isopropyltropolone, and its tyrosinase activity inhibiting capacity was examined.

The test results of said Test Example 1 and Comparative Test Example 1 are shown in FIG. 1. It will be appreciated from FIG. 1 that the liniment obtained in Test Example 1 has far higher tyrosinase activity inhibiting ability than the liniment obtained in Comparative Test Example 1.

TEST EXAMPLE 2

The compound obtained in Synthesis Example 1 was dissolved in ethanol and then pH of the solution was adjusted to 6.0 with succinic acid or potassium carbonate to obtain a liniment with a 1.0% concentration.

The tyrosinase activity inhibiting performance of this liniment was determined according to the method of Test Example 1. As control, water was used instead of said liniment and absorbance was measured in the same way.

COMPARATIVE TEST EXAMPLE 2

A liniment was prepared in the same way as Test Example 2 except that hydrogen peroxide was used instead of the compound obtained in Synthesis Example 1, and its tyrosinase activity inhibiting capacity was examined.

Figure 2:
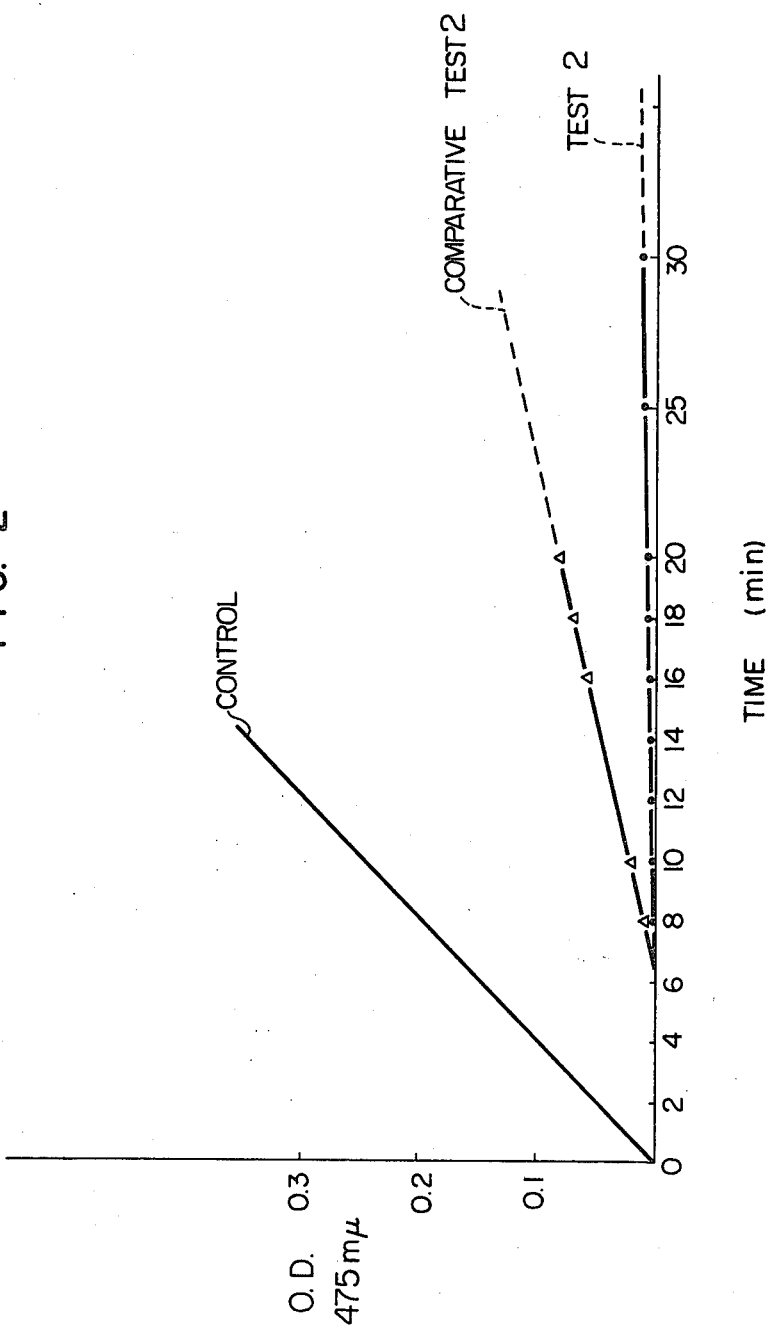
FIG. 2 is a graph showing the relation between degree of pigmentation and time for illustrating the tyrosinase activity inhibiting ability of 4-isopropyltropolone prepared by hydrolyzing the liniment obtained in Test 2 with $Na_2CO_3$.

The test results are shown in FIG. 2. It will be understood from FIG. 2 that the liniment using the compound obtained in Synthesis Example 1 is far higher in tyrosinase activity inhibiting performance than the liniment using hydrogen peroxide.

The compounds obtained in Synthesis Examples 2-5 also had a same degree of tyrosinase activity inhibitory action as the compound obtained in Synthesis Example 1.

TEST EXAMPLE 3 (Enzymatic decomposition of fatty acid ester of 4-isopropyltropolone)

(1) Substrate solution

A solution was prepared by mixing 2% of polyvinyl alcohol in an M/15 phosphate buffer (pH 7.0), and the fatty acid esters were added respectively in this solution to a concentration of 0.05 M and each solution was made into an emulsion by a homogenizer.

(2) Enzyme solution 30 mg of refined bacterial lipase was dissolved in 10 ml of water. The organ crude enzyme solution was prepared by triturating the hair-shaven skin pieces and pancreas of the rats with body weight of around 200 g and forming them into a solution.

(3) Reaction solution composition

| Composition (ml) | A | B |
|---|---|---|
| Substrate emulsion | 5.0 | 1.0 |
| Buffer | 4.0 | 1.0 |
| Refined lipase | 1.0 | — |
| Organ triturated solution | — | 2.0 |

(4) Method of measurement

After one-hour incubation at 37° C., the reaction was stopped with 5% metaphosphoric acid, and after centrifugal precipitation, the supernatant was added with 0.5 ml of a ferric chloride reagent (0.1% aqueous solution) or a ferric sulfide reagent and color development (dark red) was observed. + indicates thin red, + + indicates thick red, + + + indicates dark red, − indicates no color development, and ± indicates unconfirmed color development.

(5) Test results

The test results are shown in the following table, from which it is evident that the fatty acid esters undergo enzymatic decomposition.

| Substrate (fatty acid esters) | Bacterial lipase (refined) | Degree of formation of 4-isopropyltropolone Homogenate | |
|---|---|---|---|
| | | Rat skin | Rat pancreas |
| Acetylate | + | +++ | +++ |
| Palmitate | + | ++ | ++ |
| Stearate | + | ++ | + |

TEST EXAMPLE 4 (Effect of fatty acid esters of 4-isopropyltropolone on melanin formation in human skin)

2-palmitate and 2-stearate of 4-isopropyltropolone were used as the representative examples of the fatty acid esters of 4-isopropyltropolone, and these esters were respectively blended in a pharmacopeial hydrophilic ointment. The ointment was applied to the melasma on human face three times a day and its effect was observed with the unaided eye. The results are shown in the following table. As control, a hydrophilic ointment (prepared according to the Japanese Pharmacopeia) alone was applied to the melasma on the other side of the face in the same way as said above.

| Ointment tested | Period of application | Number of subjects | No effect | Took effect | Marvelous effect |
|---|---|---|---|---|---|
| Pharmacopeial hydrophilic ointment | 3 months | 15 | 15 | 0 | 0 |
| 0.02% 4-isopropyltropolone-2-palmitate blended ointment | 3 months | 10 | 3 | 3 | 4 |
| 0.05% 4-isopropyltropolone-2-palmitate blended ointment | 3 months | 10 | 0 | 5 | 5 |
| 0.05% 4-isopropyltropolone-2-stearate blended ointment | 3 months | 10 | 1 | 5 | 4 |

(Note)
Took effect: Obvious fading of dark color
Marvelous effect: Almost perfect disappearance of melanin.

Exemplified below are the possible prescriptions of the skin-beautifying cosmetic preparations (total amount 100 parts by weight) according to this invention. Needless to say, the invention is not limited to these prescriptions.

PRESCRIPTION EXAMPLE 1 (Lotion)

| Components | Parts by weight |
|---|---|
| 4-isopropyltropolone | 0.01 |
| Aminoacetic acid | 0.20 |
| Pyridoxine hydrochloride | 0.05 |
| EDTA | proper quantity |
| Zinc phenolsulfonate | 0.30 |
| Propylene glycol | 8.00 |
| Ethanol | 5.00 |
| Refined water | balance |
| Perfume and antiseptic | small quantities |

PRESCRIPTION EXAMPLE 2 (Pack)

| Components | Parts by weight |
|---|---|
| 4-isopropyltropolone | 0.01 |
| Stearic acid | 4.00 |

-continued

| Components | Parts by weight |
|---|---|
| Aminoacetic acid | 0.20 |
| EDTA | proper quantity |
| Zinc phenolsulfonate | 0.30 |
| Propylene glycol | 13.00 |
| Carboxyvinyl polymer | 1.20 |
| Sodium hydroxide | 0.14 |
| Ethanol | 2.50 |
| Titanium oxide | 0.02 |
| Refined water | balance |
| Perfume and antiseptic | small quantities |

PRESCRIPTION EXAMPLE 3 (Pack)

| Components | Parts by weight |
|---|---|
| 4-isopropyltropolone | 0.01 |
| Polyvinyl alcohol | 15.00 |
| Polyvinyl pyrrolidone | 4.00 |
| Stearic acid | 2.00 |
| Tween 20 | 2.00 |
| Span 60 | 0.500 |
| EDTA | proper quantity |
| Propylene glycol | 6.00 |
| Ethanol | 10.00 |
| Refined water | balance |
| Perfume and antiseptic | small quantities |

PRESCRIPTION EXAMPLE 4 (Milk lotion)

| Components | Parts by weight |
|---|---|
| 4-isopropyltropolone | 0.01 |
| Stearic acid | 2.00 |
| Cetanol | 0.50 |
| EDTA | proper quantity |
| Hydrous lanolin | 2.00 |
| Oleyl oleate | 2.00 |
| Squalane | 3.00 |
| Liquid paraffin | 8.00 |
| Emulsifier | 2.60 |
| Propylene glycol | 4.00 |
| Refined water | balance |
| Perfume, antioxidant and antiseptic | small quantities |

PRESCRIPTION EXAMPLE 5 (Vanishing cream)

| Components | Parts by weight |
|---|---|
| 4-isopropyltropolone | 0.01 |
| MC stearic acid | 8.00 |
| Beeswax | 5.00 |
| Cetanol | 3.00 |
| Hydrous lanolin | 2.00 |
| Isopropyl myristate | 6.00 |
| Liquid paraffin | 27.00 |
| Olive oil | 2.00 |
| EDTA | proper quantity |
| Emulsifier | 5.50 |
| Propylene glycol | 3.00 |
| Refined water | balance |
| Perfume, antioxidant and antiseptic | small quantities |

PRESCRIPTION EXAMPLE 6 (Cold cream)

| Components | Parts by weight |
|---|---|
| 4-isopropyltropolone | 0.01 |
| Beeswax | 10.00 |
| Ceresine | 7.00 |
| White vaseline | 3.00 |
| Hydrous lanolin | 3.00 |

-continued

| Components | Parts by weight |
|---|---|
| Isopropyl myristate | 3.00 |
| Squalane | 4.00 |
| Liquid paraffin | 40.00 |
| EDTA | proper quantity |
| Polyoxethylene cetyl ether | 2.70 |
| Emulsifier | 2.30 |
| Propylene glycol | 2.00 |
| Refined water | 23.00 |
| Perfume, antioxidant and antiseptic | small quantities |

PRESCRIPTION EXAMPLE 7 (Lotion)

| Components | Parts by weight |
|---|---|
| 2-caprylate of 4-isopropyltropolone | 0.01 |
| Aminoacetic acid | 0.20 |
| Pyridoxine hydrochloride | 0.05 |
| Zinc phenolsulfonate | 0.30 |
| Propylene glycol | 8.00 |
| Ethanol | 5.00 |
| Refined water | balance |
| Perfume and antiseptic | small quantities |

PRESCRIPTION EXAMPLE 8 (Pack)

| Components | Parts by weight |
|---|---|
| 2-butyrate of 4-isopropyltropolone | 0.01 |
| Stearic acid | 4.00 |
| Aminoacetic acid | 0.20 |
| Zinc phenolsulfonate | 0.30 |
| Propylene glycol | 13.00 |
| Carboxyvinyl polymer | 1.20 |
| Emulsifier | 3.00 |
| Ethanol | 2.50 |
| Titanium oxide | 0.02 |
| Refined water | balance |
| Perfume and antiseptic | small quantities |

PRESCRIPTION EXAMPLE 9 (Pack)

| Components | Parts by weight |
|---|---|
| 2-palmitate of 4-isopropyltropolone | 0.01 |
| Polyvinyl alcohol | 15.00 |
| Polyvinyl pyrrolidone | 4.00 |
| Stearic acid | 2.00 |
| Tween 20 | 2.00 |
| Span 60 | 0.50 |
| Propylene glycol | 6.00 |
| Ethanol | 10.00 |
| Refined water | balance |
| Perfume and antiseptic | small quantities |

PRESCRIPTION EXAMPLE 10 (Milk lotion)

| Components | Parts by weight |
|---|---|
| 2-caprylate of 4-isopropyltropolone | 0.02 |
| Stearic acid | 2.00 |
| Cetanol | 0.50 |
| Hydrous lanolin | 2.00 |
| Oleyl oleate | 2.00 |
| Squalane | 3.00 |
| Liquid paraffin | 8.00 |
| Emulsifier | 2.60 |
| Propylene glycol | 4.00 |
| Refined water | balance |

-continued

| Components | Parts by weight |
|---|---|
| Perfume, antioxidant and antiseptic | small quantities |

PRESCRIPTION EXAMPLE 11 (Vanishing cream)

| Components | Parts by weight |
|---|---|
| 2-butyrate of 4-isopropyltropolone | 0.01 |
| MC stearic acid | 8.00 |
| Beeswax | 5.00 |
| Cetanol | 3.00 |
| Hydrous lanolin | 2.00 |
| Isopropyl myristate | 6.00 |
| Liquid paraffin | 7.00 |
| Olieve oil | 2.00 |
| Emulsifier | 5.50 |
| Propylene glycol | 3.00 |
| Refined water | balance |
| Perfume, antioxidant and antiseptic | small quantities |

PRESCRIPTION EXAMPLE 12 (Cold cream)

| Components | Parts by weight |
|---|---|
| 2-palmitate of 4-isopropyltropolone | 0.01 |
| Beeswax | 10.00 |
| Ceresine | 7.00 |
| White vaseline | 3.00 |
| Hydrous lanolin | 3.00 |
| Isopropyl myristate | 3.00 |
| Squalane | 4.00 |
| Liquid paraffin | 40.00 |
| Polyoxyethylene cetyl ether | 2.70 |
| Emulsifier | 2.30 |
| Propylene glycol | 2.00 |
| Refined water | balance |
| Perfume, antioxidant and antiseptic | small quantities |

EFFECT TEST EXAMPLE 1

A panel test on the skin-beautifying effect was conducted by using a vanishing cream produced according to Prescription Example 5. Twenty woman volunteers all had facial pigmental abnormalities, and of them, 18 had spots (malesma) and 2 had freckles on their faces. In the test, said vanishing cream was applied to the right half of the face of each subject and the cream same as said above but not containing 4-isopropyltropolone was applied to the left half of the face, both being applied twice a day (morning and evening) for a period of 12 weeks.

The results showed 1 case of "salient effect", 3 cases of "noticeable effect", 10 cases of "slightly noticeable effect" and 6 cases of "little change". Thus, after all, effectiveness was confirmed on 70% of the subjects. These results imply the possibility of furthered skin-beautifying effect by continuous use of said cream for a longer period of time.

In actual applications of the composition of this invention, in case it is used as cosmetics, it is desirable to reduce the concentration of 4-isopropyltropolone or a fatty acid ester thereof, and in case it is used for the purpose of treatment of a skin disease, it is suggested to increase the concentration of said substance as far as no undesirable stimulus is given.

What is claimed is:

1. A fatty acid ester of 4-isopropyltropolone represented by the formula:

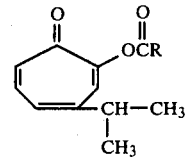

(wherein R is a hydrocarbon group having 1 to 18 carbon atoms).

2. The fatty acid esters of 4-isopropyltropolone according to claim 1, wherein said fatty acid esters are the esters of acetic acid, butyric acid, caproic acid, caprylic acid, lauric acid, myristic acid, palmitic acid, stearic acid or oleic acid.

3. A skin-beautifying cosmetic composition containing as active ingredient an effective amount of 4-isopropyltropolone having the formula:

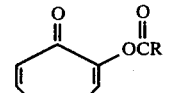

and/or fatty acid ester thereof having the formula:

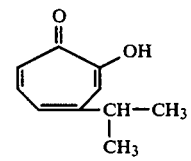

wherein R is a hydrocarbon group having 1 to 18 carbon atoms, and a cosmetic carrier.

4. The cosmetic composition according to claim 3, wherein the content of said active ingredient is 0.0001 to 10% by weight.

5. A skin-beautifying cosmetic composition containing a cosmetic carrier and as an active ingredient an effective amount of at least one member selected from the group consisting of 4-isopropyltropolone having the formula:

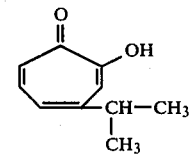

a palmitic acid ester thereof or a stearic acid ester thereof.

6. A skin-beautifying cosmetic composition containing, as an active ingredient, an effective amount of 4-isopropyltropolone having the formula:

and/or a fatty acid ester thereof having the formula:
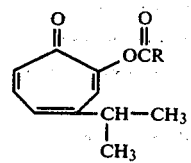
wherein R is a hydrocarbon group having 1 to 18 carbon atoms; a cosmetic carrier and a sequestering agent wherein the sequestering agent is ethylenediaminetetraacetic acid in an amount approximately 0.01 to 0.05%, based on the total weight of the composition.
* * * * *